(12) United States Patent
Brass et al.

(10) Patent No.: US 6,979,104 B2
(45) Date of Patent: Dec. 27, 2005

(54) LED INSPECTION LAMP

(75) Inventors: Jack Brass, Toronto (CA); Richard J. Doran, Wrotham Heath (GB); Donald L. Klipstein, Upper Darby, PA (US); Thomas M. Lemons, Marblehead, MA (US)

(73) Assignees: R.J. Doran & Co. LTD (GB); Brasscorp Limited (CA)

( * ) Notice: Subject to any disclaimer, the term of this patent is extended or adjusted under 35 U.S.C. 154(b) by 0 days.

(21) Appl. No.: 10/029,803

(22) Filed: Dec. 31, 2001

(65) Prior Publication Data

US 2003/0123254 A1 Jul. 3, 2003

(51) Int. Cl.$^7$ .................................... F21V 9/00

(52) U.S. Cl. ................ 362/231; 362/184; 362/244; 362/804

(58) Field of Search ........................ 362/555, 558, 362/119, 120, 187, 804, 84, 183, 184, 231, 244, 259, 800

(56) References Cited

U.S. PATENT DOCUMENTS

| | | | |
|---|---|---|---|
| 3,808,434 A | | 4/1974 | Gutiber |
| 4,185,891 A | | 1/1980 | Kaestner |
| 4,826,269 A | | 5/1989 | Streifer et al. |
| 4,935,665 A | | 6/1990 | Murata |
| 4,963,798 A | | 10/1990 | McDermott |
| 5,092,331 A | | 3/1992 | Nakamura et al. |
| 5,289,082 A | | 2/1994 | Komoto |
| 5,749,830 A | | 5/1998 | Kaneko et al. |
| 5,806,961 A | * | 9/1998 | Dalton et al. ............... 362/183 |
| 5,954,206 A | | 9/1999 | Mallon et al. ............... 209/580 |

(Continued)

FOREIGN PATENT DOCUMENTS

| | | |
|---|---|---|
| CA | 2200364 | 5/1997 |
| CA | 2200365 | 5/1997 |
| CA | 2284870 | 9/1998 |
| CA | 2280398 | 4/2000 |
| CA | 2405802 | 10/2001 |
| DE | 25 42 220 A | 3/1977 |
| DE | 299 574 A5 | 4/1992 |
| DE | 200 21 934 U1 | 4/2001 |
| DE | 201 10 813 U1 | 9/2001 |
| EP | 0 523 927 A2 | 1/1993 |
| EP | 1 059 202 A2 | 12/2000 |
| GB | 810256 | 3/1959 |
| WO | WO 98/39636 | 9/1998 |
| WO | WO 99/35486 | 7/1999 |
| WO | WO 01 52605 A2 | 7/2001 |
| WO | WO 01 81973 A1 | 11/2001 |
| WO | WO 03/004932 A1 | 1/2003 |
| WO | WO 03/02548 | 3/2003 |

OTHER PUBLICATIONS

Craig Johnson, LEDTronics FlashLED, The LED Museum, pre–Sep. 4, 2000, http://ledmusum.home.att.net/tronics.htm.

(Continued)

Primary Examiner—Alan Cariaco
Assistant Examiner—Guiyoung Lee
(74) Attorney, Agent, or Firm—Katten Muchin Rosenman LLP

(57) ABSTRACT

An LED inspection lamp has plurality of LED sources for emitting electromagnetic radiation at different peak wavelengths for causing visible fluorescence in different leak detection dyes. A lens is associated with each LED. Radiation passing through lenses is superimposed in target area at target distance. Another LED inspection lamp has plurality of LEDs emitting electromagnetic radiation at a peak wavelength. A lens adaptor has lens housing for attachment to LED inspection lamp with a single LED for causing visible fluorescence, and a lens. Substantially all of the radiation from the LED passes through the lens and is focused in a target area at a target distance from the lenses. LED spot lights have a similar configuration.

55 Claims, 7 Drawing Sheets

U.S. PATENT DOCUMENTS

| | | | |
|---|---|---|---|
| 5,975,712 | A | 11/1999 | Shiao |
| 5,984,861 | A | 11/1999 | Crowley |
| 6,095,661 | A | 8/2000 | Lebens et al. |
| 6,142,650 | A * | 11/2000 | Brown et al. ............... 362/259 |
| D434,868 | S | 12/2000 | Trigiani |
| 6,183,086 | B1 | 2/2001 | Neubert |
| 6,200,134 | B1 | 3/2001 | Kovac et al. |
| 6,250,771 | B1 | 6/2001 | Sharrah et al. |
| 6,305,818 | B1 | 10/2001 | Lebens et al. |
| 6,402,347 | B1 * | 6/2002 | Maas et al. ............... 362/294 |
| 6,468,077 | B1 | 10/2002 | Melikechi et al. |
| 6,485,160 | B1 * | 11/2002 | Sommers et al. ........... 362/184 |
| 6,491,408 | B1 * | 12/2002 | Cooper et al. ............. 362/184 |
| 6,590,220 | B1 | 7/2003 | Kalley et al. ........... 250/504 H |
| 6,710,363 | B1 | 3/2004 | Trigiani |
| 2002/0019396 | A1 | 12/2002 | Reiff et al. ................. 362/246 |
| 2003/0098425 | A1 | 5/2003 | Sosinsky |
| 2003/0123254 | A1 | 7/2003 | Brass et al. ................. 362/231 |

OTHER PUBLICATIONS

Hi–Power FlashLED(R) Flashlights, LEDTronics, Inc., date unknown, http://www.netdisty.net/ds/flt–3001/default.asp.

OSRAM SYLVANIA, Preliminary data sheet for OS–WL01A, Dated Feb. 25, 2000.

LED Museum at http://ledmuseum.home.att.net/ledleft.htm printed Feb. 27, 2002.

Product pages for Dorcy "Cool Blue" at http://www.dorcy-.com/led%20new.htm printed Feb. 27, 2002.

Saftey LED Hi–Power FlashLED Flashlights at http://secure.implex.net/NBAComputers/browse.cfm?CategoryID=8 printed Dec. 10, 2001.

Review of LEDTronics Mini–FlashLED at http://ledmuseum.home.att.net/flashled.htm printed Dec. 10, 2001.

Michael Sayer et al. Measurement, Instrumentation and Experiment Design in Physics and Engineering. Prentice-Hall of India, New Delhi, 2000, pp. 197–198. (ISBN 81–203–1269–4).

Lewis R. Koller. Ultraviolet Radiation. (2nd ed.) John Wiley & Sons, New York. 1965, pp. 158–181.

* cited by examiner

LED INSPECTION LAMP

FIELD OF THE INVENTION

This invention is related to the general field of inspection lamps for detection of fluorescent materials, and in particular to the field of inspection lamps having light emitting diodes which produce radiation suitable for exciting the fluorescent materials to be detected by such lamps.

BACKGROUND OF THE INVENTION

Detection of leaks in systems containing fluids under pressure is often accomplished by causing visible fluorescence of fluorescent dyes that are added to the fluid in the system. Such systems may be, for example, refrigeration systems where the fluid under pressure is a refrigerant and leakage results in the fluid becoming an invisible gas upon escape. The invisibility of leaked fluid can impair detection of the leak. Addition of a fluorescent dye to the refrigerant allows easier detection of leaks by illuminating possible leakage points with radiation that causes the fluorescent dye to visibly fluoresce at the site of the leak.

Leak detection by means of use of a fluorescent dye is also used in systems other than refrigeration systems, such as automotive cooling systems and in engines having a lubricant that is under pressure.

There are many inspection lamps currently available for the purpose of illuminating potential leak sites with radiation cause visible fluorescence of fluorescent dyes. It is desirable to minimize the size, weight, cost, heat production and power consumption of such inspection lamps while having adequate output from such lamps at wavelengths suitable for causing visible fluorescence of dyes used for leak detection.

Light emitting diodes (LEDs) are used as a source of light for such inspection lamps. LEDs are more efficient at producing desired wavelengths than other light sources used in such inspection lamps. LEDs are also relatively small and produce relatively little heat. Existing LED inspection lamps have had 4 LEDs in an attempt to produce sufficient intensity at a usable distance to make a fluorescent dye fluoresce. For some situations this defeats the purpose of the LED source as additional power must be consumed and the size of the lamp is increased accordingly.

In traditional inspection lamps a broadband light source is utilized, such as an incandescent or halogen bulb. This can have an advantage over LED sources as these sources have a greater radiation output, and they emit radiation over a broad spectrum that can cause a variety of fluorescent dyes to fluoresce. LEDs have a tendency to produce light only in a narrow range of wavelengths.

However, traditional lamps suffer from a number of drawbacks. The broadband light source produces mostly radiation that is not used for detection of any fluorescent dye that has frequent use for leak detection. Also, some of the radiation may be at wavelengths normally emitted by the fluorescent materials to be detected. Filters are typically used to remove such wavelengths from the output of the inspection lamp so that light from the inspection lamp does not mask fluorescence of the fluorescent material to be detected. Radiation absorbed or reflected by filters results in heat, often necessitating means to dissipate this heat.

Alternatively, inspection lamps have been produced using electric discharge light sources since such light sources are often more efficient than incandescent light sources at producing wavelengths suitable for causing visible fluorescence of materials used for leak detection. Such inspection lamps have their own disadvantages such as the cost of the special discharge light sources having sufficient intensity, the added cost of electrical components required for operation of such light sources, a requirement for some such light sources to spend time wanning up to a required elevated operating temperature in order to properly function, and the tendency of many discharge light sources to specialize in production of wavelengths not effectively utilized by all popular fluorescent dyes. There is a need to derive the full benefit of utilizing LED light sources in inspection lamps. There is also a need to retain some of the benefits of traditional light sources. It is an object of the invention to address these or other issues associated with LED inspection lamps.

SUMMARY OF THE INVENTION

In a first aspect the invention provides an inspection lamp having light emitting diodes as a source of radiation suitable for causing visible fluorescence of fluorescent materials, where said light emitting diodes are substantially non-identical in spectral characteristics of their emitted radiation, such that at least one but not all of said light emitting diodes in said inspection lamp produce wavelengths of radiation that are favorable for causing visible fluorescence of some fluorescent materials, and such that one or more different said light emitting diodes in said inspection lamp produce substantially different wavelengths of radiation which are more favorable than the wavelengths of first said light emitting diode(s) for causing visible fluorescence of some fluorescent materials other than first said fluorescent materials.

At least one light emitting diode may have a peak emission wavelength in the ultraviolet and at least one light emitting diode may have a peak emission wavelength that is visible but suitable for causing visible fluorescence of fluorescent materials.

At least one light emitting diode may produce mostly blue visible light and at least one light emitting diode may produce mostly visible violet light or ultraviolet radiation.

At least one light emitting diode may have a peak emission wavelength in the range of 425 to 480 nanometers and at least one light emitting diode may have a peak emission wavelength in the range of 360 to 430 nanometers.

The inspection lamp may have one or more lenses to collimate the radiation produced by at least some of the light emitting diodes. The radiation produced by each light emitting diode may be collimated by a separate lens associated with or mounted forward from each said light emitting diode.

The inspection lamp may have a handle. The handle may share a longitudinal axis with the inspection lamp as a whole. The handle may not share an axis with any other major portion of said inspection lamp.

The inspection lamp may accept one or more dry cells as a source of power. The inspection lamp may accept power from an external power source. The external power source may be a source of direct current with a voltage of substantially 12 volts. The external power source may be a source of alternating current with a voltage of substantially 110–125 volts. The external power source may be a source of alternating current with a voltage of substantially 220–240 volts. The inspection lamp may have one or more rechargeable cells as a source of power. The inspection lamp may have means to recharge its rechargeable cells.

The inspection lamp may have one or more dropping resistors to limit the amount of current which flows through at least one of the light emitting diodes. The inspection lamp may have non-switching current regulation means to control the amount of current which flows through at least one of the light emitting diodes. The inspection lamp may have switching current regulation means to control the amount of current which flows through at least one of the light emitting diodes. The inspection lamp may be of such design that at least one of the light emitting diodes does not require separate means to limit or control the amount of current flowing through said light emitting diode. Any of the light emitting diodes may be laser diodes. The laser diodes may be intended to normally operate in a laser mode. The laser diodes may be intended to normally operate in a non-laser mode. Oblong beams from each laser diode may be directed into different directions so as to achieve an overall beam pattern that is not oblong. The inspection lamp may have optical means to correct oblong characteristics of the beams produced by most types of laser diodes. The inspection lamp may have one more cylindrical lenses to correct oblong characteristic of the laser diodes. The inspection lamp may have optics other than cylindrical lenses to correct oblong beam characteristic of laser diodes. The inspection lamp may be of such design as to produce beams not having the oblong characteristic typical of laser diodes.

In a second aspect the invention provides a module having light emitting diodes that are substantially non-identical and which produce a variety of wavelengths suitable for exciting a variety of fluorescent dyes, and suitable for replacing the bulb and/or the reflector of a flashlight so as to achieve an inspection lamp. The inspection lamp may contain one or more of the modules.

The inspection lamp may have one or more light emitting diode modules, where at least one light emitting diode module has only one type of light emitting diode but the inspection lamp as a whole includes more than one type of light emitting diode so as to produce a variety of wavelengths suitable for exciting a variety of fluorescent dyes.

In a third aspect the invention provides an inspection lamp having two or more light emitting diodes that produce radiation suitable for causing visible fluorescence of fluorescent materials, and a lens forward from each of said light emitting diodes to collimate the radiation from each light emitting diode into a beam, such that the beams of radiation individually associated with each of said light emitting diodes project forward from said lenses and merge together.

The individual beams that project forward from each lens may be parallel to each other. The individual beams may converge towards each other such that the axes of the beams intersect with each other at a specific distance forward of the lenses. The individual beams may have an angular diameter greater than any angle between any two axes of said beams, such that some area can be illuminated by all said beams at any distance from the lenses greater than distance from the lenses to the point at which the beam axes intersect. The lenses may be comprised by a single piece of suitable transparent material. Each lens may have a center of curvature of at least one curved surface displaced from the axis of its associated light emitting diode so as to form a beam having an axis that is not parallel to said axis of said light emitting diode.

A lens assembly may have a longitudinal axis and convex lenses each having at least once curved surface with a center of curvature at a location other than on a line parallel to said lens assembly axis and passing through the center of the area of said lens, so as to be suitable as the lenses of the inspection lamp.

As stated previously for other aspects, the inspection lamp may or may not have a handle, and use a variety of internal or external power sources with or without current limiting devices.

The light emitting diodes may differ significantly in spectral characteristics so as to cause visible fluorescence from fluorescent substances which visibly fluoresce from the output of one or more but not all of said light emitting diodes.

Separate switches may be provided for each type of light emitting diode used within said inspection lamp.

At least one light emitting diode may have a peak wavelength that is ultraviolet and at least one light emitting diode may have a peak wavelength that is visible. At least one light emitting diode may have a peak wavelength less than 425 nanometers and at least one light emitting diode may have a peak wavelength greater than 425 nanometers. In a fourth aspect the invention provides an LED inspection lamp having a plurality of LED sources. Each source emits electromagnetic radiation at a different peak wavelength. Each different peak wavelength causes visible fluorescence in a different leak detection dye.

A lens may be associated with each LED so that radiation passing through all lenses from their associated LEDs is substantially superimposed to a target area at a target distance from the lenses.

In a fifth aspect the invention provides an LED inspection lamp having a single LED for emitting electromagnetic radiation at a peak wavelength for causing visible fluorescence in a leak detection dye, and a lens associated with the LED so that substantially all of the radiation passes through the lens and is substantially directed to a target area at a target distance from the lenses.

In a sixth aspect the invention provides an LED inspection lamp having a plurality of LEDs emitting electromagnetic radiation at a peak wavelength for causing visible fluorescence in a leak detection dye, and a lens associated with each LED so that the electromagnetic radiation passing through all lenses from their associated LEDs is substantially superimposed to a target area at a target distance from the lenses. In a seventh aspect the invention provides a lens adaptor having a lens housing for attachment to an LED inspection lamp with a single LED emitting electromagnetic radiation at a peak wavelength for causing visible fluorescence in a leak detection dye, and a lens within the housing. The lens and housing are associated with the LED so that substantially all of the radiation passing through the lens from the LED is substantially directed to a target area at a target distance from the lenses.

In an eighth aspect the invention provides a lens adaptor having a lens housing and lenses. The lens housing is for attaching to an LED inspection lamp with a plurality of LEDs emitting electromagnetic radiation at a peak wavelength for causing visible fluorescence in a leak detection dye. The lenses are for associating with each LED when the lens housing is attached to the inspection lamp. Radiation passing through all lenses from their associated LEDs is substantially superimposed to a target area at a target distance from the lenses.

In a ninth aspect the invention provides a lens and LED assembly for use within a flashlight casing. The assembly has a plurality of LEDs emitting electromagnetic radiation at a peak wavelength for causing visible fluorescence in a leak detection dye, and a lens associated with each LED so that the electromagnetic radiation passing through all lenses from their associated LEDs is substantially superimposed to a target area at a target distance from the lenses. The assembly is shaped to fit within the flashlight casing.

In any of the aspects a lens may be movable to permit adjustment of beam characteristics. The focal length of the lenses and the distance between the lenses (or lens assembly and the light emitting diodes) may be adjustable so as to permit changing the distance at which beam size and intensity formed by each light emitting diode and each associated lens are best-formed.

The distance between lens centers may be smaller than the distance between the centers of their associated light emitting diodes so that the beam components formed by each lens from its associated light emitting diode converge towards each other.

The beam components formed by each lens from its associated light emitting diode may converge towards each other so that all beam components coincide at a distance which can be changed by changing the location of the LEDs.

An inspection tamp may further incorporating means to restrict the possible adjustments to a range of adjustments where the beam elements are best-formed at the same distance forward from said inspection lamp at which said beam elements are coinciding with each other.

BRIEF DESCRIPTION OF THE DRAWINGS

For a better understanding of the present invention and to show more clearly how it may be carried into effect, reference will now be made, by way of example, to the accompanying drawings that show the preferred embodiment of the present invention and in which.

DETAILED DESCRIPTION OF THE PREFERRED EMBODIMENT

In this description, the term "LED source" is used. Unless the context requires otherwise, an "LED source" encompasses a single LED or a plurality of LEDs. LEDs include superluminescent diodes or laser diodes as well as conventional and other light emitting diodes. Laser diodes used in inspection lamps may be operated in a laser mode or a in a non-laser mode.

Figure 1:
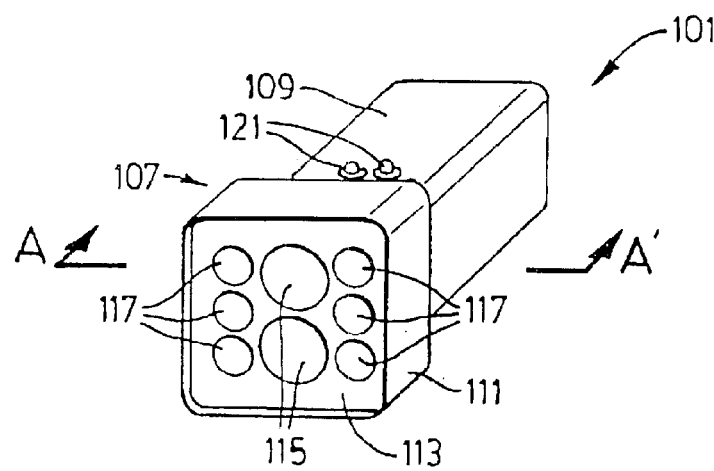
FIG. 1 is an external view showing the front, top, and left side of a lamp according to a preferred embodiment of the invention.
Figure 2:
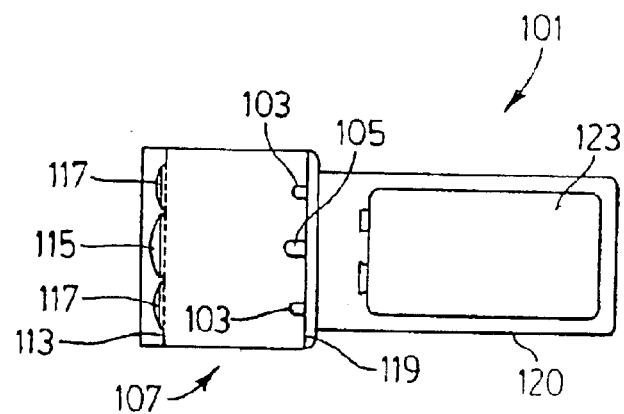
FIG. 2 is a cross sectional view through the line A–A', looking from above, of the lamp of FIG. 1.

Also, numerous variants are described. Again, unless the context requires otherwise, such variants apply equally to all of the alternative embodiments described herein. Referring to FIG. 1 and FIG. 2 an inspection lamp 101 has six light emitting diodes 103 that produce ultraviolet radiation and two light emitting diodes 105 that produce blue visible light. The diodes are placed in a configuration similar to the lenses—later introduced as 115, 117—except as otherwise set out herein. The ultraviolet light emitting diodes 103 are of a currently available type having a peak emission wavelength of 370 nanometers with a narrow beam emission permitting the smaller lens. The blue light emitting diodes 105 may be of a preferred type having a peak emission wavelength of approximately 460 nanometers, or of a more easily available type having a peak emission wavelength of approximately 470 nanometers with a wider beam emission and therefore requiring the larger lens. The number of ultraviolet light emitting diodes 103 is greater than the number of blue light emitting diodes 105 because the output power of this type of ultraviolet light emitting diode 103 is typically low compared to that of high brightness blue light emitting diodes 105.

Light emitting diodes of types and quantity different from those described may be used as they are available.

The inspection lamp 101 resembles a flashlight by having a distinct "head" section 107 attached to a distinct handle section 109, with these two sections 107, 109 sharing a common longitudinal axis.

The "head" section 107 has a head casing 111 which contains a forward bulkhead or "lens board" 113 which several lenses (115 and 117) are attached to, and which also contains a rear bulkhead or "light emitting diode board" 119, which the light emitting diodes 103, 105 are attached to. The lens board 113 is mounted sufficiently rearward from the head casing 111 for the head casing 111 to protect the lenses 115, 117 from most accidental impacts.

The head casing 111 is attached to a handle section casing 120. These two casing sections 111, 120 may be considered a single part for manufacturing purposes. The casings shown in the Figures are only examples. As will be evident to those skilled in the art, many different shapes and sizes of cases may be used. Casing design may be based on such factors as size, shape, comfort, available components, power source used, cost and visual aesthetics.

Mounted to the lens board 113 are two larger lenses 115 used to concentrate the outputs of the two visible blue light emitting diodes 105. Also mounted to the lens board 113 are six smaller lenses 117 used to concentrate and superimpose the outputs of the six ultraviolet light emitting diodes 103 to a target area at a target distance from the lenses 117. In this embodiment, all lenses 115, 117 are of the plano-convex type, with their convex surfaces facing forward, and mounted approximately their own focal lengths forward from the most forward points of their associated light emitting diodes 103, 105. Other types of lenses, such as bi-convex, meniscus (concave-convex) with similar focal lengths may be used. The plano-convex lens may have advantages in manufacturing and low sphere-related distortions of lenses where the object distance and image distance from the lenses are unequal. An asymmetrical bi-convex or meniscus lens may provide the best distortion characteristics.

It has been found for all embodiments that the target area should be greater than 1 inch wide at a target distance selected from between 5 inches and 3 feet.

For most applications, the target area is limited by the intensity of the LEDs. If the LEDs are sufficiently intense then the beam can be concentrated to a larger target area. If the LEDs are relatively weak then the beam will need to be further concentrated to a smaller target area. For clarity, the beam does not have to fall with the target area for all target distances, only for at least one target distance that is useful for the particular desired leak detection application. For the particular configurations described in this application, it has been found that a target area of approximately 2 to 7 sq. inches provides usable intensity at a usable target distance of between 4 and 20 inches. More intense LEDs or more LEDs could provide a larger target area at a useful target distance.

Lens 115, 117 mounting positions at different distances from their associated light emitting diodes 103, 105 may be favorable in use in some applications. Lens 115, 117 could be positioned at different positions forward of their associated light emitting diodes as an alternative embodiment.

Figure 6:
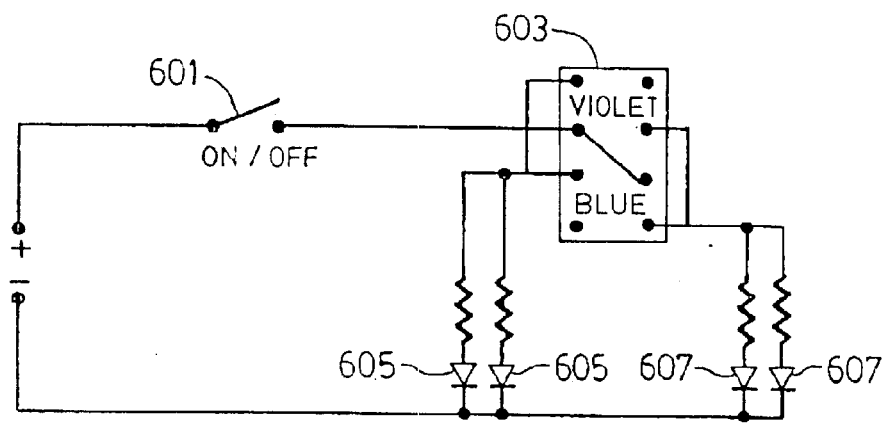
FIG. 6 is a schematic diagram of an example alternative electrical circuit for lamps according to the preferred embodiments that have multiple LED sources.
Figure 7:
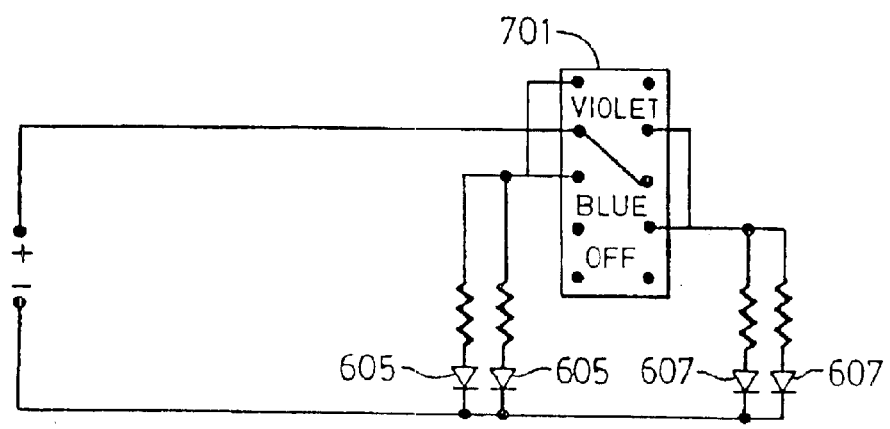
FIG. 7 is a schematic diagram of an example further alternative electrical circuit for lamps according to the preferred embodiments that have multiple LED sources.

The light emitting diode board 119 is mounted just forward of the rear surface of the head casing 111. Mounted to the light emitting diode board 119 are the two blue light emitting diodes 105 and the six ultraviolet light emitting diodes 103. Alternatively, the rear surface of the head casing 111 may be used as a surface to mount the light emitting diodes 103, 105 to, possibly eliminating the need for the light emitting diode board 119. Two momentary contact switches 121 are incorporated into this embodiment, with one to be pressed to operate the blue light emitting diodes 105 and the other to be pressed for operation of the ultraviolet light emitting diodes 103. It is permissible to press both switches 121 should it be desirable to have all of the light emitting diodes 103, 105 operating. It is possible that the operator is unaware of which dye is being used, or that the visible light from the LEDs 105 may be useful for illuminating the site being viewed while ultraviolet reactive dyes are being used, or that the radiation from one set of LEDs, for example, 103 may contain a wavelength that the fluorescent dye reacts to, even if to a lesser extent than it reacts to the wavelengths emitted by other group of LEDs 105. The light emitting diodes are powered by a battery 123 that the handle casing 119 is designed to accept. One terminal of the battery 123 would typically be connected to the cathode terminals of all of the light emitting diodes 103, 105. The other terminal of the battery 123 would typically be connected to one terminal of each of the momentary contact switches 121. The other terminal of each of these switches 121 typically connects to the anode terminals of their associated light emitting diodes 103, 109 through appropriate dropping resistors (not shown in FIG. 1 or FIG. 2; however, an examples for alternate embodiments are shown in FIG. 6 and FIG. 7).

There are several ways to properly limit the current flowing through the light emitting diodes 103, 105, including linear current regulator circuits (such as those shown in FIG. 6 and FIG. 7) and switching current regulator circuits. It is also possible to select battery types with sufficient internal resistance not to require dropping resistors or other current limiting means. Current limiting means such as dropping resistors would typically but not necessarily be mounted to the light emitting diode board 119.

Protection can be provided to accept reversed polarities, or to prevent reversed polarities from damaging the LEDs or other lamp components.

Variations of this or other embodiments may be designed to accept power from an external power source, such as an alternating current power source.

A variation of this embodiment having no lenses or lenses for only some of the light emitting diodes may be useful with light emitting diodes having adequately narrow beam characteristics.

Figure 3:
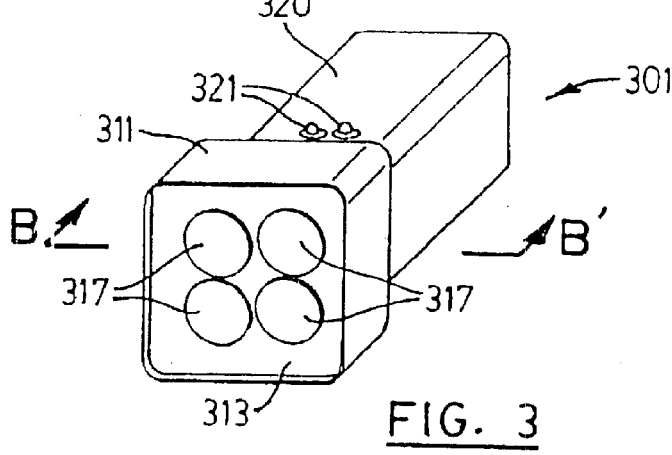
FIG. 3 is an external view showing the front, top and left side of a lamp according to an alternate preferred embodiment of the invention.
Figure 4:
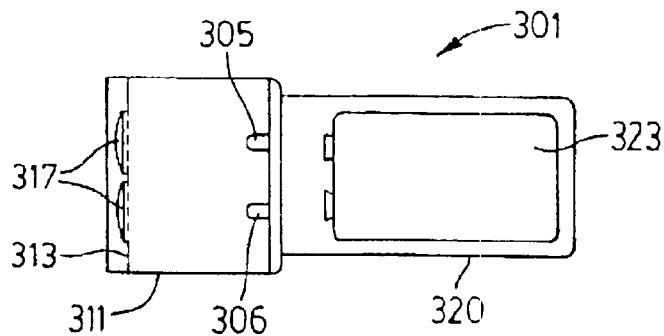
FIG. 4 is a cross sectional view through the line B–B', looking from above, of the lamp of FIG. 3.

Referring to FIG. 3 and FIG. 4 show an alternative inspection lamp 301 has two light emitting diodes 305 that produce blue visible light and two light emitting diodes 306 that produce violet visible light. Again, the LEDs each pair are lined up with one another in a similar manner to the later introduced lenses 317, except as otherwise set out herein. The blue light emitting diodes 305 are of a high output type having a peak emission wavelength in the range of 440 to 475 nanometers. The violet light emitting diodes 306 are of a high output type having a peak emission wavelength of approximately 405 nanometers. Alternatively, the shorter wavelength light emitting diodes 306 may be of an ultraviolet type having a peak emission wavelength of 395 nanometers or less while the longer wavelength light emitting diodes 305 would have a peak emission wavelength anywhere from 405 to 475 nanometers.

The lamp 301 resembles the lamp 101 by having a distinct head casing 311 and handle casing 320 sharing a common longitudinal axis so as to resemble a "flashlight". These two casing sections 311, 320 may be considered one part for manufacturing purposes. A forward bulkhead 313 or "lens board" has mounted to it four identical plano-convex lenses 317. These lenses 317 concentrate and superimpose the outputs of two blue light emitting diodes 305 and two violet light emitting diodes 306.

The blue and violet pairs of light emitting diodes 305, 306 can be activated by pressing associated momentary contact switches 321.

The handle casing section 319 accepts a battery 323 that is used to power the light emitting diodes 305, 306.

Again, current limiting means (not shown) may be dropping resistors or current regulation circuitry. Alternatively, the battery may be of a type having high enough internal resistance or other characteristics such that current regulation means is not necessary. Again, variations of this embodiment may be designed to accept power from an external power source.

Figure 5:
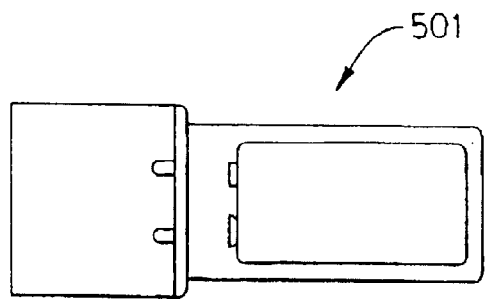
FIG. 5 is a cross sectional view looking from above of a lamp according to a further alternate preferred embodiment of the invention.

Referring to FIG. 5, a further alternate inspection lamp 501 does not use concentrating lenses, and is otherwise the same as lamp 301. In this case, the advantages of LEDs with different wavelengths are retained, and, provided the LEDs are of sufficient intensity, the resulting beam will continue to be usable in leak detection.

As intimated earlier, in any of the embodiments, it can be advantageous to utilize narrow beam LEDs. In this description a narrow beam LED is said to produce a concentrated beam. As indicated previously, a beam originating from near the focal plane of a lens will also result in a concentrated beam. When a concentrating lens is used in combination with a concentrated beam from an LED then more of the energy from the LED can be made to pass through the lens. It can be particularly useful to use a concentrated beam from an LED when a concentrating lens is not used. By directing more of the energy from the LED directly at the area to be viewed, the resulting fluorescence will be increased when compared to a wider beam from an equally powerful source. The beam area at the target site is selected to provide a usefull target area for leak detection. If the beam area is too small then portions of the system being tested may be inadvertently missed. If the beam area is too great then the intensity of the radiation at the target site may be insufficient.

If it is desired to use a particularly narrow beam LED, or an LED that has over convergent internal optics then diverging lenses may be used to create a target area sufficiently large to be usable.

Many alternate embodiments are possible, including, for example, those having only one switch to control all light emitting diodes. As another example, Embodiments of this invention may have any switching means commonly used in flashlights, such as switching means where switching is accomplished by rotating the head section. Another embodiment could include one very high power blue light emitting diode, such as a maximum current rating of 350 milliamps, along with several lower power light emitting diodes that produce visible violet light or ultraviolet radiation.

Both visible violet and ultraviolet light emitting diodes may be used in addition to the blue light emitting diode, such that light emitting diodes of more than two types are used. Alternative configurations can include any number of light emitting diodes depending on the specifications and the desired application of the lamp. When using LEDs emitting significant radiation of the same wavelength as a fluorescent dye may emit, it can be desirable to have a switch or combination of switches (such as switches 121) that allow selection of individual LEDs or groups of LEDs.

Referring to FIG. 6 and FIG. 7, other alternative switch configurations may be used, for example, a momentary switch 601 can be used in combination with an LED selector switch 603. The LED selector switch 603 selects between either LEDs 605 or LEDs 607, or both. When the momentary switch 601 is activated the currently selected LEDs will be energized. A two-pole three position switch 601 is suitable where two groups of LEDs 605, 607 are used. As an alternative example, a single switch 701 can be used to perform both the selection and activation function. A two-pole four position switch 701 is suitable where two groups of LEDs 605, 607 are used.

Figure 8:
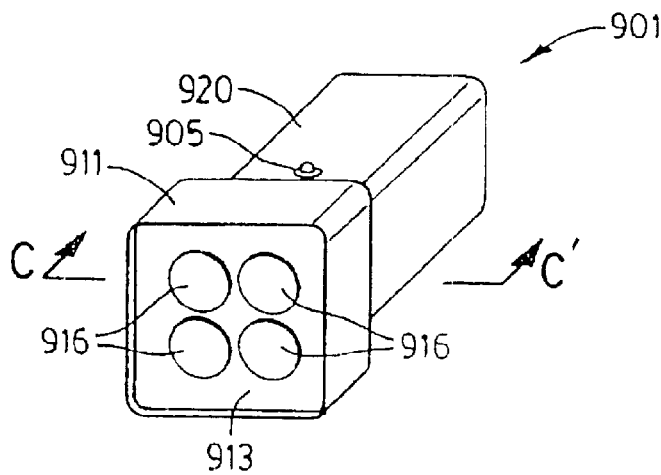
FIG. 8 is an external view showing the front, top, and left side of a lamp according to a further alternate preferred embodiment of the invention.
Figure 9:
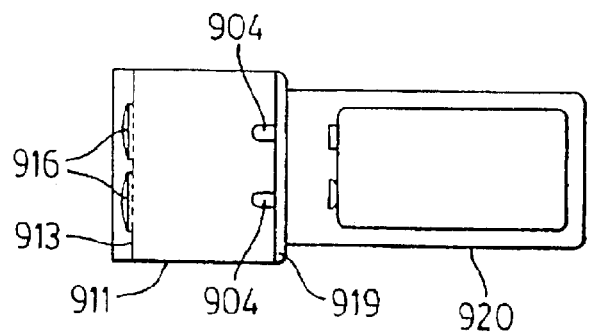
FIG. 9 is a cross sectional view through the line C–C', looking from above, of the lamp of FIG. 8.

The switches 603, 701 are 2-pole multi-position slide switches. The switch diagrams show only the fixed contacts within the switches 603, 701. The moving part of each switch 603, 701 (not shown as is often done in a slide switch wiring diagram), within the left column and repeated in the right column, connects two vertically adjacent contacts. Referring to FIG. 8 and FIG. 9 an inspection lamp 901 has four light emitting diodes 904 having a peak wavelength of anywhere from 370 to 475 nanometers. The light emitting diodes 904 may have significantly different peak wavelengths so as to excite a variety of fluorescent materials. The lamp has a single switch 905, and is otherwise similarly configured to the lamps 101, 301, with a distinct head casing 911 and handle casing 920. A forward bulkhead 913 or "lens board" has mounted to it four identical plano-convex lenses 916. These lenses 916 concentrate and superimpose the outputs of the light emitting diodes 904.

It may be important to note that in some circumstances, particularly if there is sufficient intensity, wavelengths below 395 nanometers may be harmful. Safety precautions may be necessary.

Figure 10:
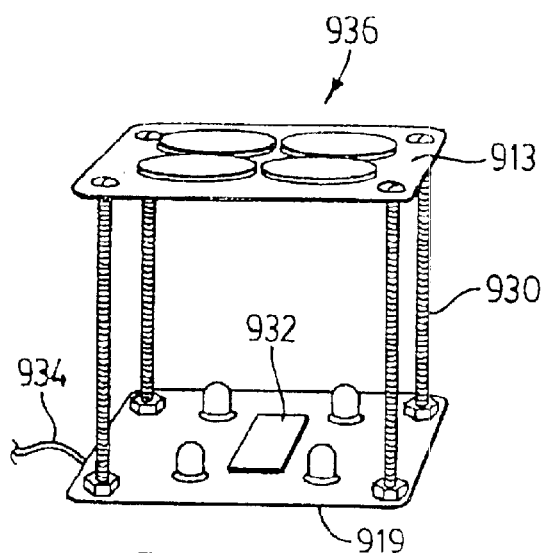
FIG. 10 is an external view showing the front, top, and left side of a lens/LED assembly according to a preferred embodiment of the invention.

Referring to FIG. 10, as an example, a lens board 913 and a LED board 919 are maintained in fixed position with respect to one another by spacers 930. Current limiting circuitry 932 is also contained on the board 919 and wire 934 is provided for connection to a battery, not shown. The other connection to the battery is by way of a button contact on the underside of the board 919. The lens board 913 and LED board 919 form lens/LED assembly 936.

A lens/LED assembly, such as the assembly 936 can replace the reflector and/or the bulb of an ordinary flashlight, not shown, in order to convert the flashlight to an inspection lamp suitable for selection of fluorescent materials. The dimensions of the assembly 936 may need to be altered in order to fit within the flashlight. For example, many flashlights are round; so, the shape of the boards 913, 919 could be made circular. All such modifications fall within the spirit and scope of the invention, the preferred embodiments of which are described herein.

In the presently preferred embodiments of the invention, the lenses are forward of the tips of the light emitting diodes. The distance from the tips of the light emitting diodes is slightly greater than the focal length of the lenses, such that each lens forms a distinct circular image of the light emitting diode at a distinct distance forward from the lenses.

The centers of the lenses are separated from each other by a distance slightly less than the distance between the centers of the light emitting diodes, such that lines from the centers of each of the light emitting diodes through the centers of their associated lenses converge at the same distance forward from the lenses that the forward portions of the bodies of the light emitting diodes are focused.

Alternatively, the lenses may be placed forward from the light emitting diodes at a distance from the tips of the light emitting diodes to the lenses that is approximately the focal length of these lenses so as to produce a smaller and more intense spot at the point of convergence.

Figure 11:
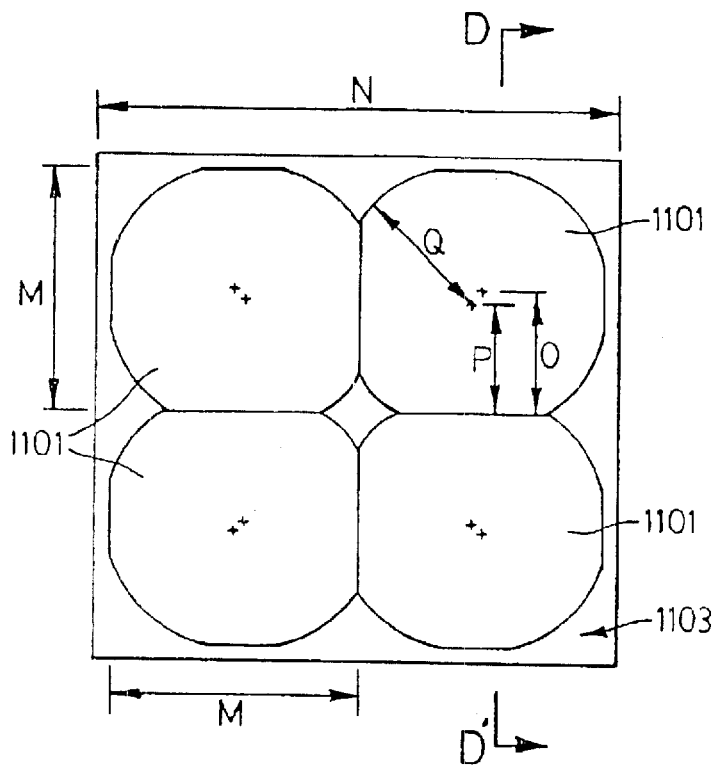
FIG. 11 is a frontal view of a lens assembly according to a preferred embodiment of the invention.
Figure 12:
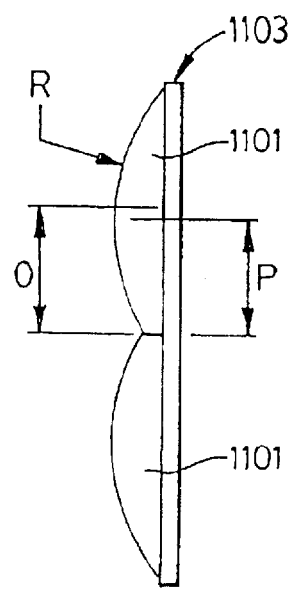
FIG. 12 is a side cross sectional view through the line D–D' of the lens assembly of FIG. 11.

Referring to FIG. 11 and FIG. 12, lenses 1101 may be formed in a lens assembly 1103 from a single moulded piece of suitable transparent material. The lenses 1101 in lens assembly 1103 are in the shape of squares with rounded corners to reduce the spacing between their centers compared to circular lenses having the same area.

Each of lenses 1101 may have its principal point displaced to one side of the center of its area so as to have some prism character. This would be done to form beams whose axes intersect at some specific distance forward of the lens assembly if each emitting diode is centered to the rear of the center of the area of each lens and the axis of each light emitting diode passes through the center of the area of each lens.

It is recognized that in any of the embodiments described herein, there may be radiation from an LED that passes through a lens other than the lens with which the LED is associated. This can result in secondary images of the LED, typically spaced around and separate from the superimposed images. Although it may be aesthetically distracting, this effect will not be detrimental to the use of the lamp. There are a number of ways to avoid this "cross-talk" between LEDs and non-associated lenses. For example, concentrated beams from LEDs could be used, separators could be placed between the LEDs, so that non-associated lenses cannot "see" other LEDs.

Referring again to FIGS. 11 and 12, in the preferred embodiment of the lens assembly 1103 width M of a lens 1101 is 13 mm, the overall width N of the lens assembly 1103 is 27.4 mm, the distance O from the centerline of the lens assembly 1103 to center between edges of each lens 1101 is 6.5 mm, the distance P from the centerline of lens assembly 1103 to center of curvature of each lens 1101 is 6 mm, the radius Q is 7.2 mm, and the radius of curvature R of each lens assuming a refractive index of 1.5 is 11.1 mm. Those skilled in the art will recognize that other combinations of parameters can be used in accordance with the principles described herein.

Figure 13:
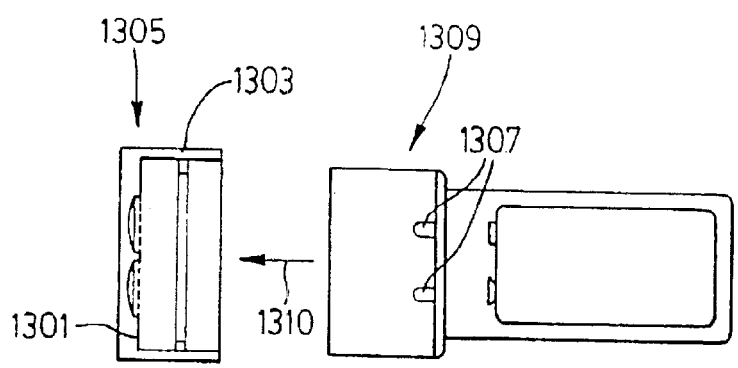
FIG. 13 is a cross-section view of a lens adapter according to a preferred embodiment of the invention in use with a multiple LED inspection lamp.

Another embodiment could be a lens assembly to be added to an existing flashlight having multiple light emitting diodes suitable for causing visible fluorescence of fluorescent materials. Referring to FIG. 13, the lens assembly 1301 could be contained in a housing 1303 to form a lens adapter 1305. In the preferred embodiment, the adapter 1305 is formed from a resilient material such as rubber, and the adapter 1305 slips over the head of an existing multiple LED 1307 lamp 1309 (as indicated by arrow 1310). The adapter 1305 has stops 1309 to assist in positioning the adapter 1305 to properly place the lens assembly 1301 in relation to the LEDs 1307. Different adapters 1305 will likely be necessary to match the particular configuration of each lamp 1309. Alternate means for removably attaching the adapter 1305 to lamp 1309 will be evident to the those skilled in the area, including, for example, a tight fitting stiff plastic for a manual fit.

Referring to FIGS. 14–18, further details of possible relationships between the lenses and LEDs will now be discussed.

Figure 14:
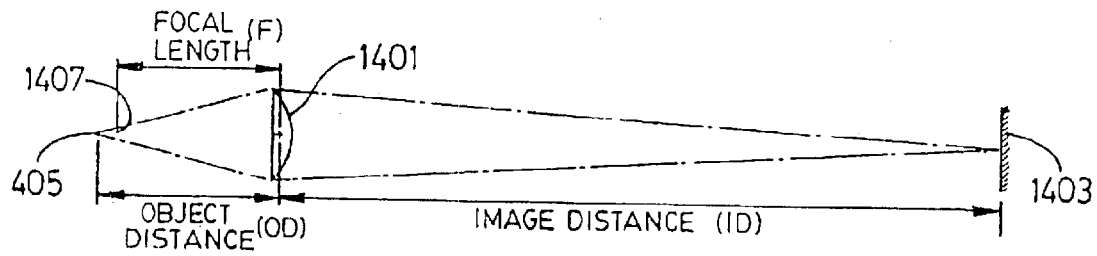
FIGS. 14–18 are ray diagram of illustrating some of the factors utilized in the preferred embodiments of the invention.

Referring to FIG. 14, a convergent lens 1401 can form an image 1403 of an object 1405. If the object 1405 is at the focal point 1407 of the lens 1401 (on one side of the lens), or at a distance (OD) from the lens 1401 equal to the focal length (F) of the lens 1401, then an image 1403 is formed at the other side of the lens 1401 at infinite distance (ID) from the lens 1401. By movement or focus of the lens 1401, the image 1403 is well-enough formed at all far distances and at any point beyond this distance the image is larger and blurred or out of focus.

There is a relationship among object 1403 distance (from the lens 1401), image distance (ID) (from the lens 1401), and focal length (F) of the lens 1401:

1/Object distance =±1/image distance =1/focal length

In the lamp 901, the lenses 916 have a focal length of 35 mm, and they are placed 40 mm from the LEDs 904 (by theory) to produce a focused image of the front surfaces of the LEDs 904 at 280 mm from the lenses 916.

Each lens of a multi-lens multi-LED flashlight, embodiments of which are described herein, makes good use of only the one LED with which it is associated. Each LED-lens combination concentrates the beam from the LED to form a "spotlight". These "spotlights" operate optically independent of each other but are aimed onto a common target and thus "superimposed"—in the case of lamp 901, 280 mm forward of the lenses was chosen as the common target distance from the lenses.

Figure 15:
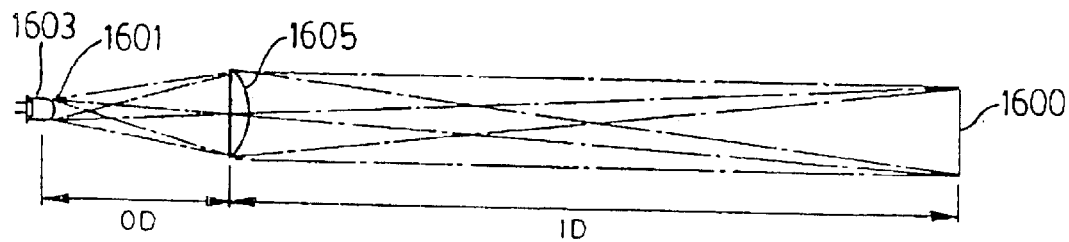

Referring to FIG. 15 ray paths involved in formation of an image 1600 of the front surface 1601 of an LED 1603 are shown. The LED 1603 is separated from lens 1605 by a distance slightly greater than the focal length of the lens 1605 and the image 1600 is formed at some distinct distance from the lens 1605. The image 1600 of the front surface 1601 of the LED 1603 is an attractive bright circle, assuming that all portions of the front surface 1601 of the LED 1603 are passing rays utilized by the lens 1605. The lamp 901 has four independent LED-lens combinations, each form a circular image onto the same area at a design "target distance" of 280 mm from the lenses 916.

Figure 16:
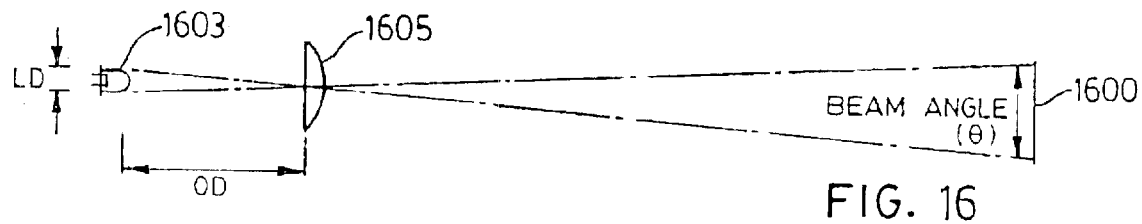

Referring to FIG. 16, rays from the edges of the LED 1603 are shown passing through the center of the lens 1605 to the edges of the image 1600, to illustrate the beam angle as a function of LED diameter (LD) and the distance (OD) from the LED 1603 to the lens 1605. Theoretically exactly, the tangent of half the beam angular diameter is equal to the ratio of LED radius (½ LD) to its distance (OD) from the lens 1605. As a useful approximation, the beam diameter in radians will usually be the ratio of LED diameter (LD) to the distance (OD) from the LED 1603 to the lens 1605. Multiplying this figure by 57.3 gives an approximate beam angular diameter in degrees.

Flashlights have a typical beam diameter of only a few degrees while many of the latest high output LEDs have a typical beam diameter of nominally 15 degrees. It has been found that a beam angular diameter less than 15 degrees is desirable for a flashlight-like sort of inspection lamp. A beam diameter of 7–8 degrees produces a spot width of about 1.5 inches at 1 foot.

In the lamp 901, the LED diameter is 5 mm and the LEDs are approx. 40 mm from the centers of the lenses. Twice the arctangent of (half of 5/40) is approx. 7.2 degrees. Thus, the beam has an angular diameter close to this where it is best-defined (best-focused and converged) approx. 280 mm from the lenses of the lamp 901.

Figure 17:
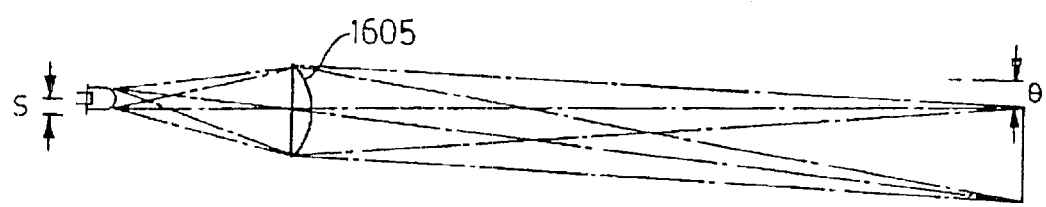

Referring to FIG. 17, shifting the LED 1603 slightly to one side (S) of the axis of the lens 1605 causes the resulting beam to form at a slight angle from the axis of the lens 1605. In the preferred embodiment of the lamp 901, the four lenses 916 are centered approx. 17.5 mm from each other vertically and horizontally, or 8.75 mm from the lens assembly's common axis vertically and horizontally.

The beams projected from each lens 916 converge onto each other at 280 mm from the lenses 916, so their centerlines deviate from the centerline of the lamp 901 so as to shift 8.75 mm vertically and horizontally from the lens axes per 280 mm of distance forward of the lenses 916.

To achieve this, the LEDs 904 are mounted in positions displaced outward from the lens axes both horizontally and vertically by (8.75*40/280) mm from the lens axes, or 1.25 mm both vertically and horizontally from the lens axes, or approx. 1.77 mm from the axes of their associated lenses 916 on lines passing through the lens assembly center, the lens axes, and the LEDs 904.

To achieve this for the preferred embodiment, the LEDs 904 are mounted in positions displaced outward from the lens 1605 axes both horizontally and vertically by (8.75*40/280) mm from the lens assembly axis or 1.25 mm both vertically and horizontally from the axes of their associated lenses 916, or approx. 1.77 mm total diagonal distance from the axes of their associated lenses 916.

Figure 18:
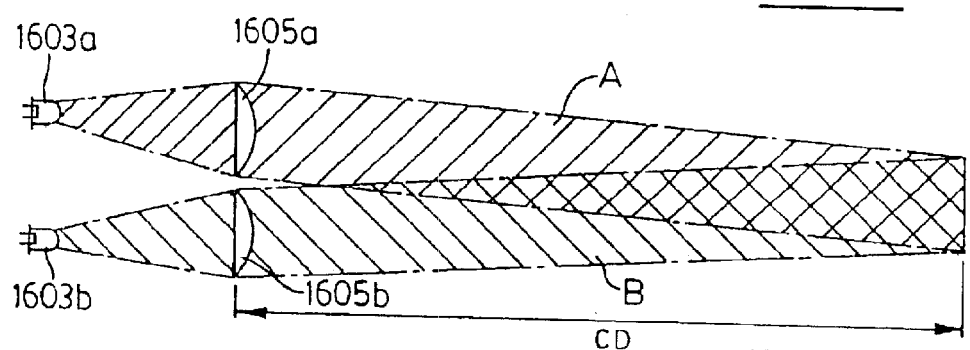

Referring to FIG. 18, two LED-lens combinations 1605a/1603a, 1605b/1603b with LEDs offset from the axes of their associated lenses produce two beams A, B that coincide at a specific distance (CD) from the lenses 1605. Not shown in FIG. 18 is rays explaining how the beams are best-defined at the same distance. However, design of a flashlight having multiple "independent units" each consisting of an LED 1603 and a lens 1605 would preferably have the beams best-defined (focused images of the front surfaces of the LEDs) at the same distance at which their centerlines intersect Although it is not strictly necessary to have a focused image, it minimizes light wasted into a less illuminated "blur zone". Another advantage of a beam with sharp edges is that a sharp beam edge makes it easier to determine whether or not an area being inspected is being illuminated by the beam.

The above explains how a multi-lens multi-LED flashlight produces a beam which is attractive and impressive at a specific distance from the lenses. It is desirable to have as wide a range of useful "working distance" as possible.

Generally, a shorter lens focal length compared to the "typical working distance" or "design working distance" results in the beams being well-defined over a wider range of distances. However, a shorter focal length results in a wider beam. This can be countered by use of smaller diameter LEDs to the extent such smaller LEDs are available. The "usual size" of LED is 5 mm (often known in the USA as "T1-¾"), with the next-most-common size being 3 mm (often known in the USA as "T1").

Another consideration is that the smaller the lens area required to utilize the beam is, the less the beam loses definition at distances other than the target area. Smaller size LEDs lose most of their advantage here, since they are generally not available in beam width as narrow as that of narrow beam versions of larger LEDs. The main effect of the relationship between LED size and narrowest available beamwidth is to largely set a preferred minimum lens diameter of approx. 13 mm to produce a roughly 7–8 degree beam.

However, the shorter focal length of lenses to be used with smaller diameter LEDs is advantageous in having individual beams from each lens retaining good definition over a wider range of distances—to the extent that suitable LEDs are available in the smaller size.

One more consideration is making the lines passing through the center of the LEDs and the "principal point" of its associated lens to have the least possible angle of convergence. This makes the beams largely coincide with each other over a larger range of distances. One way to make the beam axes have a reduced angle of convergence is to use smaller diameter lenses.

However, the lenses must be large enough to catch most of the output beams of the LEDs. Narrower beam LEDs are advantageous here.

It should be noted that most 5 mm LEDs have significant light output to 7.5–8 degrees from the LED axis, or in other words have a 15–16 degree beam. 5 mm LEDs with substantially narrower beamwidth have significant output outside their nominal beam area, often as a "secondary ring beam" 15–18 degrees in angular diameter. 3 mm LEDs have nearly proportionately wider beams, and permit only a small reduction in lens diameter.

One more consideration is that the angular diameter of each beam exiting a lens should exceed the angle between axes of the beams. Achieving this assures that all individual beams merge into each other at least partially for all distances from about half the "design target distance" to infinite distance.

The angle between beam centers, in degrees, is approximately 57.3 times the ratio of lens spacing (between centers of lenses in opposite corners of the lens assembly) to design target distance from the lens. This figure for the preferred embodiment of lamp 901 is 57.3 times (25/280) or approx. 5.1 degrees. Since this figure is less than the approx. 7.2 degree diameter of the individual beams, there is some area covered by all beams at all distances greater than the design target distance. If this is true, then generally it is also true that all distances as short as approx. half the design target distance can be illuminated by all of the individual beams.

As noted above with respect to FIG. 18, usual convex lenses 1605 in a usual configuration require the LEDs 1603 to be offset vertically and horizontally from the axes of the lenses 1605. A disadvantage of this is that the LEDs 1603 must be slightly tilted to be aimed at the centers of the lenses 1605 (which is done in the lamp 901) or the lenses 1605 must be large enough to capture "off-center" LED beams.

If the lenses 1605 have a "prismatic effect" of bending a ray passing through the center of the area of the lens, then the LED 1603 can be mounted directly behind the lens 1605 with the LED 1603 and lens 1605 having a common axis parallel to that of an inspection lamp. The lens 1605 would then form a beam which exits the lens 1605 at an angle from the axis of the lens 1605.

One way to achieve this is to use a plano-convex lens having the center of curvature offset slightly from a "centerline" parallel to the axis of the entire "flashlight unit" and passing through the center of the area of the lens. One possible arrangement is that each lens is 16.8 mm wide and the LEDs coincide with lens axis/centerlines 16.8 mm apart but the centers of the curvature of the curved lens surfaces are only 14.7 mm apart. LEDs 40 mm from such lens elements would form beams bent after exiting from these lens elements so as to coincide with each other 280 mm from the lenses.

Referring to FIG. 12, one can see how the center of curvature of each lens 1101 is offset slightly from the center of the area of the lens 1101.

As otherwise described herein, a lens specification in an inspection lamp having a lens forward of each LED can be determined as follows:

1. For a given target distance and beam width to design for, the LED's distance from the lens would be the LED's diameter times the ratio of target distance to beam width at the target distance.
2. The lens focal length should be:

$$1/(1/(\text{target distance from lens}) + 1/(\text{LED distance from lens}))$$

3. The lens or lens should be barely wide enough to capture the beam produced by the LED. Multiply the LED's distance from the lens by twice the tangent of half the beam angle, and add to this the LED's diameter. (Or determine experimentally how wide a lens is required to capture the LED's beam at the distance from the LED that the lens is to be located at.)

Most 5 mm narrow beam LEDs have a beam width, including any significant secondary beam features, of approx. 15–18 degrees. Most 3 mm narrow beam LEDs have an overall beamwidth of approx. 25–28 degrees. These are the presently preferred LEDs.

4. Then comes the offset between LED axis and lens axis to make the beams converge:
   a) In the prototype shown in FIG. 10, ordinary convex lenses (with optical center coinciding with the center of the area of each lens) are used and the centers of the LEDs are spaced slightly further apart than the centers of the lenses such that rays from the lens centers pass through the lens centers unbent and converge upon the center of the target area. The LEDs would be angled to aim them at the lens centers.
   b) A variation of this embodiment would have the lens centers closer together than the LED centers, but the LEDs are not aimed at the lens centers. The lenses would then need to be wide enough to capture the beams from the LEDs. This means that the lens radius needs to exceed the beam radius by the offset between the LED's axis and the axis of the lens in order for the lens to capture the beam.

c) Lenses with optical center offset from the midpoint of the lens can be used. Each LED can be directly behind the midpoint of the lens, but the optical center (center of curvature of curved surfaces) is offset from the midpoint of the lens (or lens element) so that a ray passing through the midpoint of the lens is bent. FIG. 12 shows a molded assembly of such lens elements.

Figure 19:
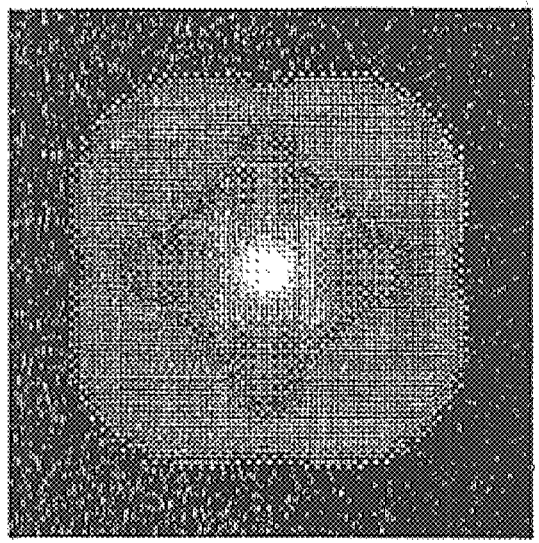
FIG. 19 is an image of the lamp of FIG. 8 at 6 inches.
Figure 20:
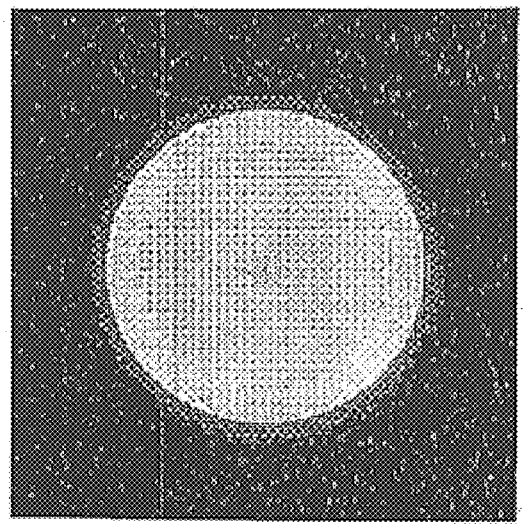
FIG. 20 is an image of the lamp of FIG. 8 at 11 inches.
Figure 21:
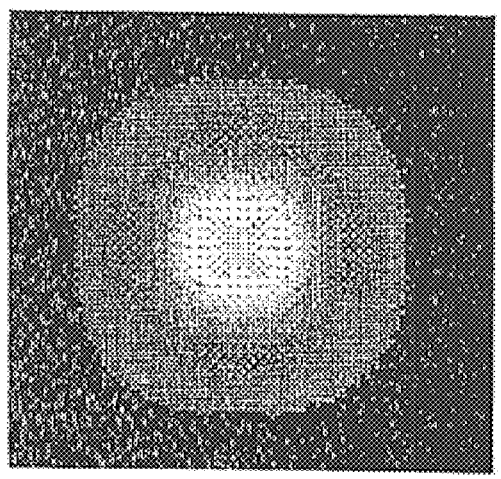
FIG. 21 is an image of the lamp of FIG. 8 at 20 inches.

Referring to FIGS. 19–21, the benefits of concentrating and superimposing lenses can be seen. Referring to FIG. 19, at a target distance of 6 inches a beam 2103 formed with lamp 901 is concentrated and partially superimposed.

Referring to FIG. 20, at 11 inches, the beam 2103 is well-defined (focused, concentrated and superimposed) in a given area. At this distance, the beam width was approximately 36 mm.

Referring to FIG. 21, at 20 inches the beam 2103 remains concentrated in a limited area. Although the beam is substantially superimposed, convergence is not perfect at this distance. Beam divergence spreads the beam to an ever increasing area which reduces the beam intensity.

Figure 22:
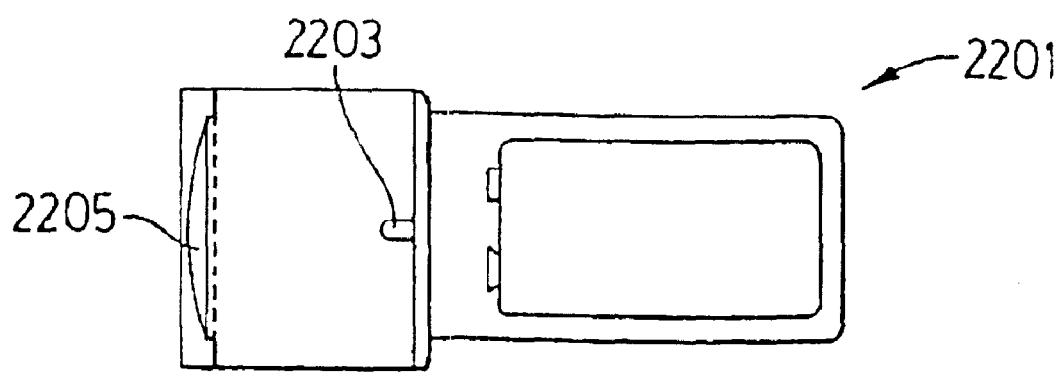
FIG. 22 is a cross sectional view looking from above of a lamp according to a further alternate preferred embodiment of the invention.

Referring to FIG. 22, a lamp 2201 has a single LED 2203 and a single converging lens 2205. The LED 2203 has a peak wavelength that is useful with a leak detection fluorescent dye, for example any of the LEDs previously mentioned could be used. The LED 2203 and lens 2205 combination is configured similarly to any one of the LED and associated lens combinations described previously; however, it is not necessary to offset the LED 2203 from the axis of the lens 2205, or to offset the principle point of the lens 2205, as the beam does not need to be superimposed on other beams. The lamp 2201 provides a more intense, concentrated beam than a single LED 2203 without such a lens.

The lamp 2201 can be more compact than if multiple LEDs and lenses are used. The lamp 2201 can have useful battery life operating from a single "watch" type of battery. For LEDs having particularly wide beams it is desirable to use the shortest possible focal length lens such as a plastic fresnel or pair of simple lenses. Some high power LEDs, for example 350 milliamps, are only available in wide beam angle, for example approximately 100 degrees. In a preferred embodiment of this configuration the diameter of the lens should approximate the focal length of the lens.

LEDs typically have a rated operating life of approximately 100,000 hours. Leak detection lamps are typically operated sporadically for relatively short periods. All embodiments can be configured to drive LEDs at a greater wattage then their rated wattage ("overdrive"). This will reduce the lifetime of the LEDs, but will increase the intensity of the emitted radiation.

It may be appropriate to allow the lenses in a LED inspection lamp to be movable. For example, moving or focusing a lens assembly will permit some adjustment of beam convergence. The amount of adjustment in a multiple lens assembly may be limited since reduction of the distance from the LEDs and the lens assembly may eventually cause the lenses not to capture all of the light from each LED. As a further example, adjusting the distance between the LEDs and the lenses can adjust the distance at which the beams are in focus.

It is also possible to create inspection lamps with multiple LEDs where only some of the LEDs have lenses. The LEDs not associated with lenses should be separated from LEDs associated with lenses by a sufficiently large distance (typically at least a lens diameter) so that lenses do not block the beams of LEDs that do not have lenses in front of them. It will be understood by those skilled in the art that this description is made with reference to the preferred embodiment and that it is possible to make other embodiments employing the principles of the invention which fall within its spirit and scope as defined by the following claims. For example, one or more LEDs of differing beamwidth may be used. The beams do not have to be focused at the target distance. The beams may be different from one another in width or other characteristics. It may be advantageous for beams of different wavelengths to have different target areas and/or a different target distance. Any of the lenses may be fresnel lenses.

LED inspection lamps may use non-conventional LEDs such as superluminescent diodes or laser diodes.

Laser diodes used in inspection lamps may be operated in a laser mode or a non-laser mode. Laser diodes used in inspection lamps may be of types whose main application would be an associated generation of optical media which would require blue or violet laser diodes. Inspection lamps having laser diodes may have cylindrical lenses or other optics which would correct the oblong beam shape that most laser diodes have. Alternatively, laser diode beams may be collimated with non-cylindrical lenses in a scheme where non-cylindrical lenses are used to achieve a desired beam pattern.

We claim:

1. An inspection lamp having:
   a. Two or more light emitting diodes which produce radiation suitable for causing visible fluorescence of fluorescent materials,
   b. A plurality of lenses, a lens of the plurality of lenses forward from each of said light emitting diodes to collimate the radiation from each light emitting diode into a beam, such that each beam of radiation individually associated with each of said light emitting diodes projects forward from its lens and a plurality of beams of radiation simultaneously produced by a plurality of the light emitting diodes merge together, wherein the individual beams converge towards each other such that the axes of the beams intersect with each other at a specific distance forward of the lenses, and wherein the individual beams have an angular diameter greater than any angle between any two axes of said beams, such that some area can be illuminated by all said beams at any distance from the lenses greater than distance from the lenses to the point at which the beam axes intersect.

2. An inspection lamp as set forth in claim 1 where the lenses are comprised by a single piece of suitable transparent material.

3. An inspection lamp as set forth in claim 1 having a handle.

4. An inspection lamp as set forth in claim 3 where the handle shares a longitudinal axis with the inspection lamp as a whole.

5. An inspection lamp as set forth in claim 3 where the handle does not share an axis with any other major portion of said inspection lamp.

6. An inspection lamp as set forth in claim 1 designed to accept one or more dry cells as a source of power.

7. An inspection lamp as set forth in claim 1 designed to accept power from an external power source.

8. An inspection lamp as set forth in claim 7 where the external power source is a source of direct current with a voltage of substantially 12 volts.

9. An inspection lamp as set forth in claim 7 where the external power source is a source of alternating current with a voltage of substantially 110–125 volts.

10. An inspection lamp as set forth in claim 7 where the external power source is a source of alternating current with a voltage of substantially 220–240 volts.

11. An inspection lamp as set forth in claim 1 having one or more rechargeable cells as a source of power.

12. An inspection lamp as set forth in claim 11 further having means to recharge its rechargeable cells.

13. An inspection lamp as set forth in claim 1 having dropping resistors to limit the amount of current that flows through at least one of the light emitting diodes.

14. An inspection lamp as set forth in claim 1 having non-switching current regulation means to control the amount of current which flows through at least one of the light emitting diodes.

15. An inspection lamp as set forth in claim 1 having switching current regulation means to control the amount of current which flows through at least one of the light emitting diodes.

16. An inspection lamp as set forth in claim 1 of such design that at least one of the light emitting diodes does not require separate means to limit or control the amount of current flowing through said light emitting diode.

17. An inspection lamp as set forth in claim 1 where the light emitting diodes differ significantly in spectral characteristics so as to cause visible fluorescence from fluorescent substances which visibly fluoresce from the output of one or more but not all of said light emitting diodes.

18. An inspection lamp as set forth in claim 17 where at least one light emitting diode has a peak wavelength shorter than 425 nanometers and at least one light emitting diode has a peak wavelength longer than 425 nanometers.

19. An inspection lamp as set forth in claim 17 having separate switches for each type of light emitting diode comprised within said inspection lamp.

20. An inspection lamp as set forth in claim 1 having at least one light emitting diode with a peak wavelength less than 425 nanometers and at least one light emitting diode with a peak wavelength greater than 425 nanometers.

21. An inspection lamp as set forth in claim 1 where the lenses are part of a lens assembly that is movable to permit adjustment of beam characteristics.

22. An inspection lamp as set forth in claim 21 wherein the distance between the lens assembly and the light emitting diodes is adjustable so as to permit changing the distance at which beam components formed by each light emitting diode and each associated lens element are best-formed.

23. An inspection lamp as set forth in claim 21 where the LED locations can be changed to permit adjustment of the angle at which beam elements formed by each lens of the lens assembly converge towards each other.

24. An inspection lamp having:
  a. Two or more light emitting diodes which produce radiation suitable for causing visible fluorescence of fluorescent materials,
  b. A plurality of lenses, a lens of the plurality of lenses forward from each of said light emitting diodes to collimate the radiation from each light emitting diode into a beam, such that each beam of radiation individually associated with each of said light emitting diodes projects forward from its lens and a plurality of beams of radiation simultaneously produced by a plurality of the light emitting diodes merge together, wherein the individual beams converge towards each other such that the axes of the beams intersect with each other at a specific distance forward of the lenses, and wherein each lens has an area and a center of curvature of at least one curved surface displaced from the axis of its associated light emitting diode so as to form a beam having an axis that is not parallel to said axis of said light emitting diode.

25. A lens assembly having a longitudinal axis and convex lenses each having at least one curved surface with a center of curvature at a location other than on a line parallel to said lens assembly axis and passing through the center of the area of said lens, so as to be suitable to comprise the lenses of an inspection lamp as set forth in claim 24.

26. An inspection lamp as set forth in claim 24 where the lenses are comprised by a single piece of suitable transparent material.

27. An inspection lamp as set forth in claim 24 having a handle.

28. An inspection lamp as set forth in claim 27 where the handle shares a longitudinal axis with the inspection lamp as a whole.

29. An inspection lamp as set forth in claim 27 where the handle does not share an axis with any other major portion of said inspection lamp.

30. An inspection lamp as set forth in claim 24 designed to accept one or more dry cells as a source of power.

31. An inspection lamp as set forth in claim 24 designed to accept power from an external power source.

32. An inspection lamp as set forth in claim 31 where the external power source is a source of direct current with a voltage of substantially 12 volts.

33. An inspection lamp as set forth in claim 31 where the external power source is a source of alternating current with a voltage of substantially 110–125 volts.

34. An inspection lamp as set forth in claim 31 where the external power source is a source of alternating current with a voltage of substantially 220–240 volts.

35. An inspection lamp as set forth in claim 24 having one or more rechargeable cells as a source of power.

36. An inspection lamp as set forth in claim 35 further having means to recharge its rechargeable cells.

37. An inspection lamp as set forth in claim 24 having dropping resistors to limit the amount of current that flows through at least one of the light emitting diodes.

38. An inspection lamp as set forth in claim 24 having non-switching current regulation means to control the amount of current which flows through at least one of the light emitting diodes.

39. An inspection lamp as set forth in claim 24 having switching current regulation means to control the amount of current which flows through at least one of the light emitting diodes.

40. An inspection lamp as set forth in claim 24 of such design that at least one of the light emitting diodes does not require separate means to limit or control the amount of current flowing through said light emitting diode.

41. An inspection lamp as set forth in claim 24 where the light emitting diodes differ significantly in spectral characteristics so as to cause visible fluorescence from fluorescent substances which visibly fluoresce from the output of one or more but not all of said light emitting diodes.

42. An inspection lamp as set forth in claim 41 where at least one light emitting diode has a peak wavelength shorter than 425 nanometers and at least one light emitting diode has a peak wavelength longer than 425 nanometers.

43. An inspection lamp as set forth in claim 41 having separate switches for each type of light emitting diode comprised within said inspection lamp.

44. An inspection lamp as set forth in claim 24 having at least one light emitting diode with a peak wavelength less than 425 nanometers and at least one light emitting diode with a peak wavelength greater than 425 nanometers.

45. An inspection lamp as set forth in claim 24 where the lenses are part of a lens assembly that is movable to permit adjustment of beam characteristics.

46. An inspection lamp as set forth in claim 45 wherein the distance between the lens assembly and the light emitting diodes is adjustable so as to permit changing the distance at which beam components formed by each light emitting diode and each associated lens element are best-formed.

47. An inspection lamp as set forth in claim 45 where the LED locations can be changed to permit adjustment of the angle at which beam elements formed by each lens of the lens assembly converge towards each other.

48. A lens adaptor, comprising: a lens housing and a plurality of lenses, the lens housing for attachment to an LED inspection lamp with a plurality of LEDs emitting electromagnetic radiation at a peak wavelength for causing visible fluorescence in a leak detection dye, and each lens of the plurality of lenses is associated with a respective one of the LEDs when the lens housing is attached to the inspection lamp to collimate the radiation from each LED into a beam, such that each beam of radiation individually associated with each of said LEDs projects forward from its lens and a plurality of beams of radiation simultaneously produced by a plurality of the LEDs merge together, wherein the individual beams converge towards each other such that the axes of the beams intersect with each other at a specific distance forward of the lenses, and wherein the individual beams have an angular diameter greater than any angle between any two axes of said beams, such that some area can be illuminated by all said beams at any distance from the lenses greater than distance from the lenses to the point at which the beam axes intersect.

49. A lens and LED assembly for use within a flashlight casing, the assembly comprising: a plurality of LEDs emitting electromagnetic radiation at a peak wavelength for causing visible fluorescence in a leak detection dye, and a plurality of lenses, each lens of the plurality of lenses is associated with a respective one of the LEDs to collimate the radiation from each LED into a beam, such that each beam of radiation individually associated with each of said LEDs projects forward from its lens and a plurality of beams of radiation simultaneously produced by a plurality of the LEDs merge together, wherein the individual beams converge towards each other such that the axes of the beams intersect with each other at a specific distance forward of the lenses, and wherein the individual beams have an angular diameter greater than any angle between any two axes of said beams, such that some area can be illuminated by all said beams at any distance from the lenses greater than distance from the lenses to the point at which the beam axes intersect.

50. An inspection lamp having:
a. Two or more light emitting diodes which produce radiation suitable for causing visible fluorescence of fluorescent materials,
b. A plurality of lenses, a lens of the plurality of lenses forward from each of said light emitting diodes to collimate the radiation from each light emitting diode into a beam, such that each beam of radiation individually associated with each of said light emitting diodes projects forward from its lens and a plurality of beams of radiation simultaneously produced by a plurality of the light emitting diodes merge together, wherein the lenses are part of a lens assembly that is movable to permit adjustment of beam characteristics, wherein the LED locations can be changed to permit adjustment of the angle at which beam components formed by each lens of the lens assembly converge towards each other, and wherein the distance between lens centers is smaller than the distance between the centers of the light emitting diodes that the lenses are forward from so that the beam components, formed by each lens from the light emitting diode that the lens is forward from, converge towards each other.

51. An inspection lamp as set forth in claim 50 where the beam components formed by each lens from its associated light emitting diode converge towards each other so that all beam components coincide at a distance which can be changed by changing the locations of the LEDs.

52. An inspection lamp as set forth in claim 51 where the distance between the lens assembly and the light emitting diodes is adjustable so as to permit adjustment of the distance at which beam components are focused in addition to permitting adjustment of the distance at which beam elements are coinciding with each other.

53. An inspection lamp as set forth in claim 52 further incorporating means to restrict the possible adjustments to a range of adjustments where the beam elements are best-formed at the same distance forward from said inspection lamp at which said beam elements are coinciding with each other.

54. A lens adaptor, comprising: a lens housing and a plurality of lenses, the lens housing for attachment to an LED inspection lamp with a plurality of LEDs emitting electromagnetic radiation at a peak wavelength for causing visible fluorescence in a leak detection dye, and each lens of the plurality of lenses is associated with a respective one of the LEDs when the lens housing is attached to the inspection lamp to collimate the radiation from each LED into a beam, such that each beam of radiation individually associated with each of said LEDs projects forward from its lens and a plurality of beams of radiation simultaneously produced by a plurality of the LEDs merge together,
wherein the individual beams converge towards each other such that the axes of the beams intersect with each other at a specific distance forward of the lenses, and wherein the individual beams have an angular diameter greater than any angle between any two axes of said beams, such that some area can be illuminated by all said beams at any distance from the lenses greater than distance from the lenses to the point at which the beam axes intersect.

55. A lens and LED assembly for use within a flashlight casing, the assembly comprising: a plurality of LEDs emitting electromagnetic radiation at a peak wavelength for causing visible fluorescence in a leak detection dye, and a plurality of lenses, each lens of the plurality of lenses is associated with a respective one of the LEDs to collimate the radiation from each LED into a beam, such that each beam of radiation individually associated with each of said LEDs projects forward from its lens and a plurality of beams of radiation simultaneously produced by a plurality of the LEDs merge together, wherein the individual beams converge towards each other such that the axes of the beams intersect with each other at a specific distance forward of the lenses, and wherein the individual beams have an angular diameter greater than any angle between any two axes of said beams, such that some area can be illuminated by all said beams at any distance from the lenses greater than distance from the lenses to the point at which the beam axes intersect.

* * * * *